US005240922A

United States Patent [19]

O'Neill

[11] Patent Number: 5,240,922

[45] Date of Patent: Aug. 31, 1993

[54] FERTILITY ENHANCEMENT

[75] Inventor: Christopher O'Neill, Greenwich, Australia

[73] Assignee: Northern Sydney Area Health Service, New South Wales, Australia

[21] Appl. No.: 778,879

[22] PCT Filed: May 7, 1990

[86] PCT No.: PCT/AU90/00183

§ 371 Date: Dec. 27, 1991

§ 102(e) Date: Dec. 27, 1991

[87] PCT Pub. No.: WO90/13299

PCT Pub. Date: Nov. 15, 1990

[30] Foreign Application Priority Data

May 5, 1989 [AU] Australia .............................. PJ5054

[51] Int. Cl.[5] ..................... A01N 43/00; A01N 43/62; A01N 37/34

[52] U.S. Cl. .................................... 514/211; 514/219; 514/220; 514/523

[58] Field of Search ................ 514/77, 220, 219, 211, 514/523

[56] References Cited

PUBLICATIONS

CA 112(13), Milligan et al, "Failure of platelet activating factor to induce decidualization . . . ".

CA 109(21), Spinks et al, "Antagonists of embryo derived PAF prevent implantation . . . ".

CA 110(9), O'Neill, "Composition and methods for fertility control using PAF . . . ".

CA 108(25), Acker et al "Role of PAF in the oviplantation in the rat . . . ".

Biology of Reproduction, "Effects of Indomethacin and ICI 46,474 Administered During Ovum Transport on Fertility in Rabbits", vol. 14, No. 4, May 1976, pp. 451–457.

Acta Endocrinologica, "Prostaglandin E2: Analysis of Effects on Pregnancy and Corpus Luteum in Hamsters and Rats", vol. 71, supplement 170, 1972, pp. 3–32.

*Primary Examiner*—Marianne M. Cintins

*Assistant Examiner*—Rebecca Cook

*Attorney, Agent, or Firm*—Lowe, Price, LeBlanc & Becker

[57] ABSTRACT

The present invention relates to a method of enhancing implantation of an embryo within the uterus of a female mammal. The method comprises administering an amount of a PAF antagonist, effective to enhance implantation, to the mammal. The invention also relates to a method of increasing the level of PAF around an embryo in the uterus of a female mammal by administering an amount of a PAF antagonist sufficient to inhibit PAF catabolism. Desirably the PAF antagonist is administered together with PAF or a homologue or analogue thereof. The invention also provides compositions comprising a PAF antagonist together with PAF or a homologue or analogue thereof, and a process for preparing the same.

21 Claims, 9 Drawing Sheets

CPM(----)
4000
3000
2000
1000
SF
PE
PC
SPH
LPC
3H-PAF
3H-LPAF
0.002 A.U. 203 nm
10
20
30
40
ELUTION TIME IN MINUTES

FERTILITY ENHANCEMENT

TECHNICAL FIELD

The present invention relates to methods of enhancing fertility in mammals, in particular to increasing the implantation potential of embryos within the uterus following in vivo or in vitro pre-implantation development.

BACKGROUND ART

It is now thought that a major cause of infertility and subfertility in humans arises due to failure of implantation of the fertilised embryo within the uterus. Implantation failure also contributes to the difficulties encountered in in-vitro fertilisation programmes and in animal breeding.

Although hormonal manipulation is effective in certain selected cases, at present there is no uniformly successful therapy available to address this problem.

Australian Patent Application No 77189/87, relates to the discovery that the fertility of mammals can be controlled by causing artificial changes to the level (or activity) of the ether phospholipid Platelet Activating Factor (PAF) which is produced and secreted by mammalian embryos. Specifically the above application discloses that such changes can result in a contraceptive effect or fertility enhancement. The specification states that "to increase the chance of implantation it was necessary to increase the in vivo concentration of PAF, usually by the artificial addition of exogenous PAF or PAF analogue or by reducing the rate of destruction of PAF by acetylhydrolase" during the pre and peri-implantation period.

An increase in PAF concentration can be easily achieved in vitro simply by adding synthetic PAF. In vivo this is more difficult. Adding PAF to biological fluids results in its very rapid deactivation by serum acetylhydrolase and other systems. This fluid phase catabolism seems not to be of great significance for embryo-derived PAF since the evidence to date shows that it is bound, probably to a protein carrier, in such a manner as to make it not readily susceptible to the action of serum acetylhydrolase. The predominant route of embryo-derived PAF catabolism therefore is via cellular catabolism.

This route is thought to involve the binding of PAF to its plasma membrane receptor, and on cellular activation the PAF is internalised and cytosolic acetylhydrolase converts it to lyso-PAF followed soon after by the action of acyltransferase which leads to the production of a long chain acyl alkyl glycerophosphocholine which is not active biologically.

It is possible to overcome the lability of exogenously added PAF by the use of PAF analogues that have biological activity, but which are not susceptible to hydrolysis. A number of these have been reported but the one most fully studied to date is a carbamyl derivative. This compound is quite resistant to the actions of acetylhydrolase. Another alternative is to use embryo-derived PAF that has been generated in vitro and which is in a bound form and thus non-hydrolysable. This is a real possibility but the cost of production is likely to be prohibitive. Both of these approaches have the disadvantage that administration of exogenous PAF can be dangerous. It is a potent mediator of anaphylaxis and allergic responses. Therefore the systemic administration of PAF must be performed extremely carefully.

Local administration of PAF into the uterus does not appear to expose the mother to these dangers (at least in the mouse and the sheep). Local administration of PAF however is of only limited therapeutic practicality, systemic administration is by far the most desirable.

The present invention comes from the entirely unexpected observation that a variety of pharmacological inhibitors of PAF activity have a bi-phasic effect on the establishment of pregnancy. At low dose (the dose where they are first effective at inhibiting the action of PAF) they inhibit implantation in both the mouse and rat. This effect reaches a maximum and further increases, (by as little as 4–10 fold concentration) result in a loss of this contragestational action and enhancement of implantation. This is entirely unexpected because for all other PAF mediated patho-physiological events investigated to date, the actions of the pharmacological inhibitors of PAF are active at even massive doses. In no cases in the literature of which the inventor is aware is there evidence for such apparent partial agonism. Recent data has shown that PAF receptor antagonists act to inhibit the cellular catabolism of PAF. This has been demonstrated to occur for at least the platelet, neutrophil and endothelium.

To date this effect has only been shown to occur for PAF receptor antagonists however and it has been proposed that the action is to prevent binding of PAF to its receptor and hence limit the amount of PAF that is internalised. The present invention shows that this phenomenon is not limited to receptor antagonists, in fact, a number of classes of pharmacological inhibitors of PAF also inhibit PAF catabolism. This inhibitory activity for all classes of compounds investigated occurred at concentrations somewhat higher than that which inhibited the cell activating effects of PAF. Thus, the pharmacological action would appear to be that at a low dose the agents inhibit PAF activation of cells but at a higher dose they also limit the catabolism of PAF. The result would therefore be a tendency for the build up of PAF. In most patho-physiological cases the PAF would be susceptible to fluid phase catabolism and therefore there is little net effect on the antagonistic action of these agents. In the case of embryo-derived PAF however the PAF is in a form that is not readily catabolised in the fluid phase and therefore a localised build up in the concentration of PAF would result. The inventor has now shown that the primary site of action of PAF on embryos is on the embryo itself in a positive autocrine manner, this localised build up results in PAF out-competing the inhibitors effects on the embryo and causing enhancement of fertility.

Apart from the reduction in catabolism of PAF, and the consequent increase in its local concentration, there is an associated benefit. The high concentration of antagonists in the body means that the systemic actions of PAF are suppressed. Therefore, PAF can be administered exogenously without the normal deleterious side effects. This systemic administration helps in elevating the local concentration of PAF in the reproductive tract and hence fertility.

Thus the present invention relates specifically to fertility enhancement, and in one aspect provides a novel way of overcoming the practical problems of the prior art involved in the use of PAF or analogues thereof for the enhancement of fertility.

OBJECTS OF INVENTION

It is thus an object of the present invention to provide novel methods of fertility enhancement.

DESCRIPTION OF THE INVENTION

In AU 77189/87 it is disclosed that the administration of a PAF antagonist causes an artificial reduction in PAF concentration around the fertilised embryo or artificial inhibition of PAF-mediated pathways involved in embryo cell division and/or implantation. The present invention is based on the surprising discovery that at high doses PAF antagonists appear to limit the catabolism of PAF and give rise to an enhancement of implantation.

The invention therefore provides a method of enhancing implantation of an embryo within the uterus of a female mammal which method comprises administering to said mammal an effective implantation enhancing amount of a PAF antagonist.

The invention also provides a method of enhancing implantation of an embryo within the uterus of a female mammal, which method comprises administering to said mammal an effective implantation enhancing amount of a PAF antagonist together with PAF, or a homologue or analogue thereof, wherein the antagonist is administered systemically and the PAF is administered systemically or locally.

Desirably the treatment should be administered during the pre- and peri-implantation period of pregnancy.

Thus in a further embodiment the invention provides a method of enhancing implantation of an embryo within the uterus of a female mammal which method comprises administering to said mammal an effective implantation enhancing amount of a PAF antagonist, together with PAF or a homologue or analogue thereof, during the pre- and peri-implantation period of pregnancy wherein the antagonist is administered systemically and PAF is administered systemically or locally.

In an alternative embodiment of the invention the invention provides a method of increasing the level of PAF around an embryo in the uterus of a female mammal, which method comprises administering to the mammal an amount of a PAF antagonist sufficient to inhibit PAF catabolism.

In a further embodiment the invention provides a composition for enhancing implantation comprising a PAF antagonist together with PAF or a homologue or analogue thereof.

In accordance with the invention fertility can be enhanced in all mammals. The invention is especially useful in enhancing fertility in humans, bovines, ovines, equines, porcines, caprines, canines, and felines. Furthermore, the invention applies to enhancement of embryo implantation within the uterus following in vivo or in vitro pre-implantation embryo development.

It is proposed that the invention will apply to the following groups of PAF antagonists a) Naturally occurring PAF antagonists, e.g. kadsurenone, dihydrokadsurenone, the structural analogue L652 731, or the tetrahydrothiophene analogue L653 150, fargesin a lignan isolated from Magnolia fargesii, or the Ginkgolides A,B,C,M and T (derived from Ginko Biloba) such as BN 52021, BN 52020 or BN 52022. Also included are factors obtained from the fermentation of certain fungi and microorganisms e.g. FR 900452 (*S. phacofaciens*) FR-49175 (*P. testikowski*) or FR 106969 (*P. citrinum*), Burseran (a 3,4-disubstituted tetrahydrofuran isolated from *Bursera microphylla* A) or the 2,3,4-trisubstituted tetrahydrofuran magnosalicin (BN 52004) isolated from *Magnolia salicifolia*, or L-652469 isolated from *Tussilago farfara* L.

b) Prostaglandins and prostaglandin analogues, e.g. $PGE_2$, OP-1206 (a $PGE_1$ analogue) or Iloprost (an analogue of $PGI_2$).

c) Non-steroidal anti-inflammatory agents, e.g. phenylbutazone, sulfinpyrazone, indomethacin or 1-(4'-R-phenyl-methylene)indenes particularly the E-(trans) derivatives.

d) PAF related structures, such as inactive PAF analogues which effectively block PAF binding sites on the platelet cell membrane. Included are charged PAF antagonists which contain a positive charge in the form of a zwitterion or quaternary alkyl or heterocyclic group. These antagonists may be classified as open-chain PAF analogues or cyclic PAF analogues.

Examples of open-chain PAF analogues include CV-3988, CV-6209, or ONO-6240, RO-18-7953, RO-19-1400, RO-18-8736, or RO-19 3704, (Hoffmann-La Roche), RU 45703 (Hoeschst-Roussel), SRI 64-557 or SRI 63-119 (Sandoz), GS 1065-180 or GS 1160-180 (Ciba-Geigy).

Examples of cyclic analogues of PAF are: SRI 63-072, SRI 63-441, SRI 62-412, SRI 62-586, SRI 63-675 or SRI 63-073 (Sandoz), BN 55009 or BN 52111.

e) Synthetic PAF antagonists, e.g. triazolobenzodiazepine derivatives such as Alprazolam, Triazolam or the structurally related WEB 2086 or WEB 2170 (Boehringer Ingelheim), or STY 2108. Also useful are the s-triazolo[3,4-c]-thieno[2,3-e][1,4]diazepines such as Brotizolam, or Etizolam, 48740 RP or 52770 RP (Rhone-Poulenc) or the calcium antagonists diltiazem or verapamil.

Further agents which exhibit PAF antagonist activity may be found in W. J. Houlihan, Platelet-Activating Factor Antagonists, Inflammatory Disease & Therapy, Marcel Dekker Inc and D. Hosford et al., PAF-receptor antagonists, chapter 4, Frontiers in Pharmacology and Therapeutics, Blackwell Scientific; the disclosures of which are incorporated herein by reference.

Whilst members of all the above groups of PAF antagonists may be effective in the method of the invention, preferred antagonists will be those that are the most specific in their action at the lowest dose. Thus the more preferred antagonists are WEB 2170 and WEB 2086.

Embryo-derived PAF has been shown to share apparent homology with 1-0-alkyl-2-acetyl-sn-glyceryl-3-phosphocholine (PAF-acether).

Further PAF receptor agonists are set out in J. Godfroid et al, PAF Receptor Agonists, Structure-Activity Relationships, Platelet-Activating Factor in Endotoxin and Immune Diseases, Sandoz Research Institute; the disclosure of which is incorporated herein by reference.

The period of treatment will obviously vary according to the species involved, thus in humans treatment would preferably be administered on days 1–7 and in sheep on days 1–16 of pregnancy.

The effective amounts of antagonists required will differ according to their mechanism of action, and pharmacokinetics, and according to the species to be treated, but in practice concentrations greater than those producing a contragestational action will be necessary. Generally increases in concentration of up to approximately 10 fold over those producing a contragestational effect will be effective in the method of the invention, with increases in concentration of 4–5 fold being preferred.

The formulations of the invention may be administered by the normal routes at sufficient doses to maintain adequate concentrations of the active components at the site of action. To maintain consistent levels of the active components systemic administration is preferred, in once or twice daily doses.

Routes of administration, doses of active ingredients, and frequency of administrations are all factors which can be optimized using ordinary skill in the art.

DESCRIPTION OF THE PREFERRED EMBODIMENTS

Figure 1:
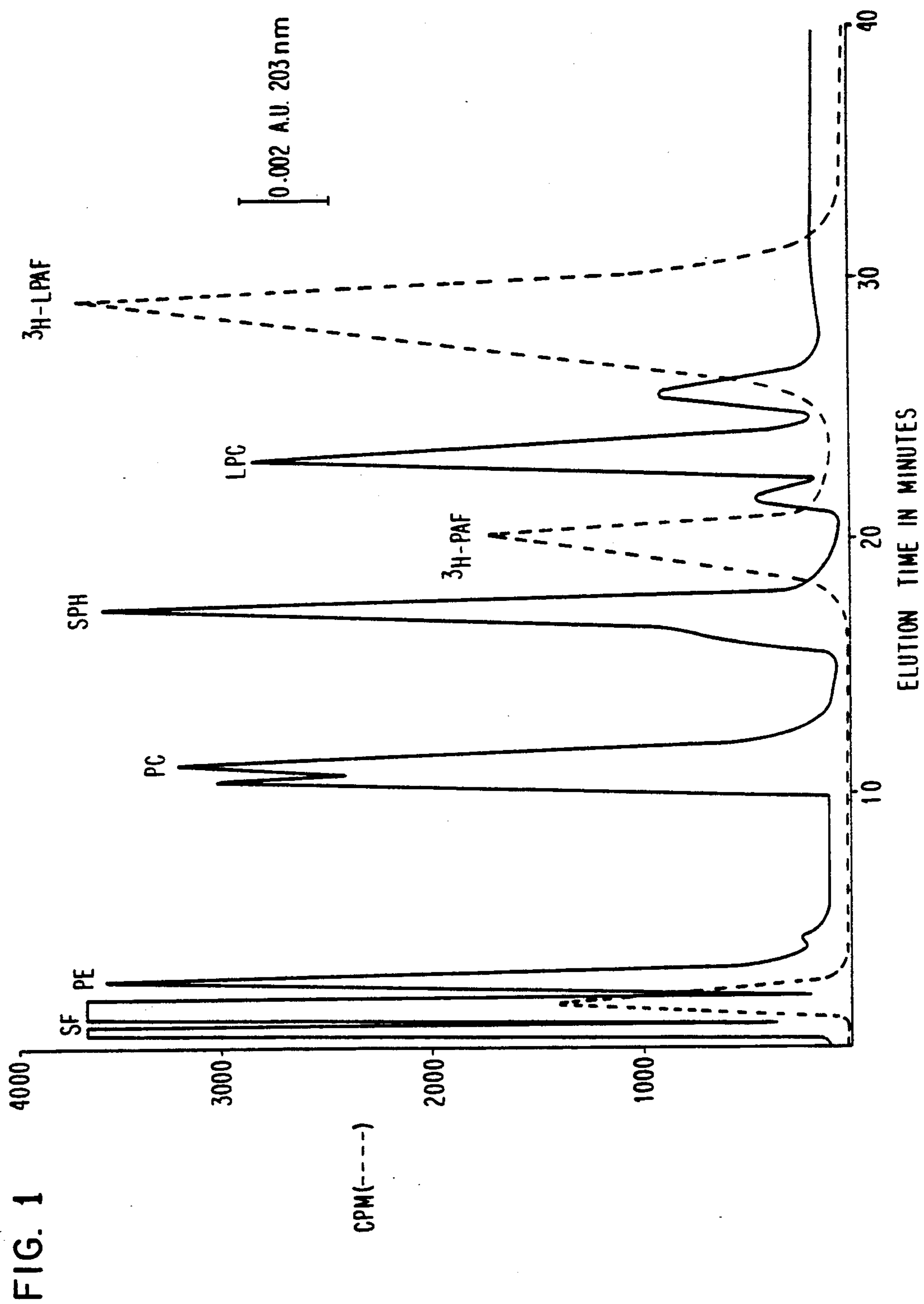
FIG. 1, shows a chromatogram, with the elution time of a number of common phospholipids and the profile of elution of $^3$H-PAF and $^3$H-Lyso PAF.

The new invention relates specifically to the enhancement of fertility by reducing cell associated catabolism of PAF. This can be achieved by any pharmacological means which prevent PAF induced cellular activation. The results predict that for any agent that has anti-PAF activity at a dose range close to its anti-PAF catabolic activity, then administration of such agent will allow (a) some fertility enhancing effects when administered on its own at an appropriately high dose, and (b) the harmless co-administration of exogenous PAF that will also have fertility enhancing effects.

In performing the method of the invention PAF antagonists have been administered as intraperitioneal injections, however, similar results have been found after intravenous and subcutaneous administration of antagonists. It is thus inferred from this that the route of administration is not important as long as the appropriate concentration of antagonists is maintained. Similarly, the time course of administration has been found to be of little apparent consequence. For instance, 1 dose of 80 μg/day of WEB 2086 seems to have the same effect as 2×40 μg/day. Thus the appropriate regimen will be discovered empirically for each compound depending on its metabolic half-life and its clearance rate in each species of interest, the only requirement apparently is that the dose be maintained at a high level. If the dose is allowed to drop to a lower level over a significant period of time then it is expected that the concentration of the antagonist would slip into the antagonistic range. Results from giving antagonists on various single days only (i.e. D1 or D2 or D3 or D4 in mice) have shown that if given only on the first days of pregnancy the agents have little effect. If given only on day 3 or particularly on day 4 (the day implantation is initiated in mice) then treatment is partially effective but that the most effective treatment is administration throughout this period. In the case of mice effective doses of the antagonists were found to be approximately in the range of 50–100 μg/day of WEB 2086, 40–80 μg/day of SRI 63 441, or 20–40 μg/day of Iloprost.

The compositions according to the invention can be prepared by uniformly mixing an effective amount of the active components with a pharmaceutically acceptable carrier or excipient. The carrier can take a wide range of forms in accordance with a desirable medicament form for the administration. These medicament compositions are desirably in a unit dosage form suitable for oral administration or injection. In the preparation of a composition in the oral dosage form, any useful, pharmaceutically acceptable carrier can be used. For example, an oral liquid preparation such as a suspended medicament or syrup medicament can be prepared using water; sugars such as sucrose, sorbitol, fructose, etc.; glycols such as polyethylene glycol, propylene glycol, etc.; oils such as sesame oil, olive oil, soybean oil, etc.; and flavors such as strawberry flavor, peppermint, etc. Powder, pills, capsules and tablets can be prepared using an excipient such as lactose, glucose, sucrose, mannitol, etc.; a disintegrator such as starch, sodium alginate etc.; a lubricant such as magnesium stearate, talc, etc.; a binder such as polyvinyl alcohol, hydroxypropylcellulose, gelatin, etc.; a surfactant such as fatty acid esters; and a plasticizer such as glycerine, etc. Tablets and capsules are the most useful, oral unit dosage forms because of easy administration. To prepare tablets and capsules, solid carriers for medicament are used. Injection solution can be prepared using a carrier consisting of distilled water, a salt solution, a glucose solution or a mixture of the salt solution and the glucose solution.

The formulations may also be in the form of sustained release preparations, which may be administered orally, or by injection as a dispersion in a pharmaceutically and pharmacologically acceptable liquid vehicle.

Suppositories for rectal, vaginal or uterine administration of the active components can be prepared by mixing the drug with a suitable nonirritating excipient such as cocoa butter and polyethylene glycols which are solid at ordinary temperatures but liquid at the rectal or vaginal temperature and will therefore melt at the site and release the drug.

The invention will now be further described by reference to the following non-limiting examples.

EXAMPLE 1

The following example demonstrates the capacity of the PAF receptor antagonists SRI 63-441, Iloprost and aspirin to inhibit catabolism of PAF.

Preparation of Platelets

Blood (0.8 vol) from a male New Zealand white rabbit was collected into 3.2% (w/v) tri-sodium citrate (4° C. 0.2 vol. The platelets were centrifuged at 100 g for 15 min to produce platelet rich plasma. They were then washed three times in Tyrodes buffer containing ACD (9:1) (pH 6.4). After the last wash the platelets were resuspended ($250\times10^3$/mm) in Tyrodes buffer (13.7 mM NaCl, 2.6 mM KCl, 11.9 mM $CO_3$, 1.0 mM Mg $Cl_2$, 0.41 mM $NaH_2PO_4$, 0.5 mM Dextrose, and 5.0 mM Hepes) containing 0.25% bovine serum albumin (CSL. Melbourne, Australia) (pH 7.4) (Tyrodes-BSA).

$^3$H-PAF and Inhibitors $^3$H-PAF was obtained from New England Nuclear (NEN). $^3$H-PAF in chloroform was placed into siliconized glass test tubes. Solvent was evaporated under $N_2$ and PAF was resuspended in Tyrodes-BSA. The inhibitors SRI 63-441, and Aspirin were prepared as stock solutions in Tyrodes-BSA and Iloprost stock was as supplied by Schering AG. 0.1 mg Iloprost/ml saline. To produce the concentration of inhibitors required serial dilution was performed with Tyrodes-BSA.

Catabolism Assay

The washed platelet suspension (250 μl) were placed into a 37° C. teflon chambers and stirred using magnetic flea. 5 μl of $^3$H-PAF in Tyrodes-BSA was added to give a final concentration of 1.3 nM and immediately after this 10 μl of Tyrodes-BSA containing appropriate concentrations of inhibitors was added. For 0 time assessment, 125 μl of the platelet suspension was added immediately to 19 vols of methanol to stop catabolism. Further samples were cultured at various times thereafter and the reaction stopped.

Lipid Extraction

The platelet suspension (1 vol) was deproteinised by addition to 19 vol of methanol. The precipitate was removed by centrifugation and to the methanol (1 vol) was added $H_2O$: Chloroform 0.8: 0.95 (v/v) to effect phase separation. The chloroform phase was reduced to a residue in a rotary evaporator and then resuspended in 100 μl of methanol. The lipid fraction was then chromatographed by HPLC.

Chromatography

Ion exchange chromatography was performed to separate PAF from its metabolites. An LKB system was used with a 250×4.6 mm Partisil SCX (covalently bound benzene sulphonate residues) 10 μm silica (Whatman). The mobile phase was $CH_3CN:CH_3OH:H_2O$ (300:150:35 (v/v) with a flow rate of 1.5 ml/min. 1.5 ml fractions were collected for 40 mins and the radioactivity in each fraction counted by scintillation counting. FIG. 1 shows a typical chromatogram with the elution time of a number of common phospholipids and the profile of elution of $^3$H-PAF and $^3$H-Lyso PAF. The acyl derivative of PAF eluted approximately 11–12 minutes, PAF at 18–21 mins and Lyso-PAF 28–31 mins. In all experiments performed over 85% of all counts recovered occurred in these three regions. Counts eluting with the solvent front were generally less than 10%.

Figure 2:
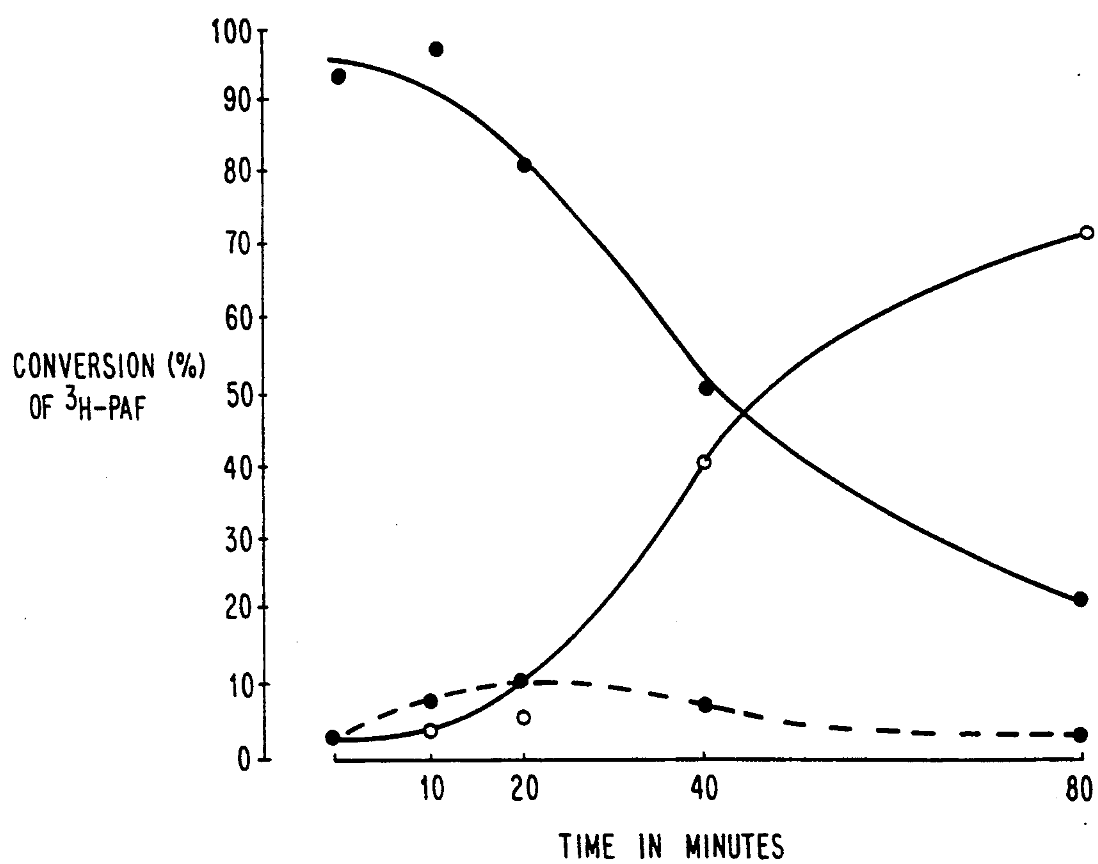
FIG. 2, shows the time response of catabolism of PAF by washed platelets. ○——○ represents Lyso-PAF, ●——● represents PAF and ●- - - -● represents a long chain acyl.

The first experiment was performed in the absence of any PAF antagonist. FIG. 2 shows the time response of catabolism of PAF by washed platelets. A significant degree of bioconversion of PAF had occurred by 15 mins by which time most of the converted PAF could be found in the lyso-PAF fraction. Catabolism continued in an almost linear fashion till 80 minutes. From 15 minutes on the majority of PAF was converted to the long chain acyl phosphocholine derivative of PAF and at 80 mins there was no significant levels of lyso-PAF present, confirming that lyso-PAF does not accumulate as a significant metabolite in platelets. For further experiments 80 mins was used as an end point and the percent conversion of $^3$H-PAF to acyl alkyl glycerophosphocholine used as the measure of catabolic activity.

Table 1 shows that the PAF receptor antagonist SRI 63-441 significantly reduced catabolism of $^3$H-PAF. At a dose of 13 nM there was a slight but not significant reduction in the catabolism, this was very great at the 130 nM and reached a maximum at 1300 nM. This was a consistent observation over a number of different replicates.

Similar results occurred for Iloprost. At 2.5 nM there was a modest but not significant inhibition of catabolism, at this dose there was considerable variability between replicates such that in some replicates there was marked inhibition. At 26 nM maximum inhibition of catabolism occurred and further increases in the concentration of PAF had no further inhibitory effect.

Aspirin had no effect on PAF catabolism in the nM range. At 2.77 nM (close to the maximum dose of Aspirin achievable in solution) caused a modest reduction in catabolism.

TABLE 1

SUMMARY OF PAF CONVERSION IN PRESENCE OF SRI 63-441

% Conversion to P.C. at 80 mins

| | Dose (nM) | | | | |
|---|---|---|---|---|---|
| | 0 | 13 | 130 | 1,300 | 13,000 |
| | 73.3 | 58.2 | 47.9 | 13.3 | 36.9 |
| | 73.5 | 61.9 | 25.3 | 24.7 | 9.1 |
| | 61.8 | | 54.1 | 18.5 | 11.8 |
| | 69.4 | | 28.0 | 21.9 | 30.1 |
| X | 69.5 | 60.1 | 38.8 | 19.6 | 22.0 |
| SD | 5.5 | — | 14.3 | 4.9 | 13.6 |
| SE | 2.7 | — | 7.2 | 2.5 | 6.8 |
| N | 4 | 2 | 4 | 4 | 4 |

All 0 time % PC less than 5%

TABLE 2

ILOPROST

Summary of PAF Conversion in Presence of Iloprost

% Conversion to P.C. at 80 mins

| | Dose (nM) | | | | |
|---|---|---|---|---|---|
| | 0 | 2.6 | 26 | 260 | 2600 |
| X | 64.7 | 52.8 | 38.5 | 41.4 | 48.8 |
| SD | 4.8 | 18.9 | 3.8 | 4.4 | — |
| SE | 2.1 | 9.4 | 1.6 | 1.8 | — |
| N | 5 | 4 | 6 | 5 | 2 |

P.C. at 0 time was always less than 4%

TABLE 3

SUMMARY OF PAF CONVERSION IN PRESENCE OF ASA

| | % Conversion to P.C. at 80 mins | | | |
|---|---|---|---|---|
| Dose (mM) | 0 | 0.55 | 1.39 | 2.77 |
| x | 73.4 | 79.7 | 72.7 | 55.6 |
| SD | 10.2 | 3.4 | 6.9 | 12.8 |
| SE | 5.9 | 2.0 | 3.5 | 6.4 |
| | **% Conversion to Lyso-PAF @ 80 min** | | | |
| Dose (mM) | 0 | 0.5 | 1.39 | 2.77 |
| x | 12.9 | 3.6 | 3.9 | 5.4 |
| SD | 17.5 | 1.0 | 1.5 | 2.0 |
| SE | 10.1 | 0.6 | 0.8 | 1.0 |

EXAMPLE 2

The study was repeated using the PAF receptor antagonists SRI 63-441 and WEB 2086 to inhibit catabolism of PAF by washed rabbit platelets. Since other platelet activators can also promote catabolism of PAF by platelets the ability of the $PGI_2$ stable analogue, Iloprost (Zk 36374) (which inhibits platelet activation by all agonists studied) to also inhibit the catabolism of PAF was studied.

Preparation of Platelets

The method employed was essentially the same as described in Example 1.

$^3$H-PAF and Inhibitors $^3$H-PAF was obtained and prepared as in Example 1. SRI 63-441 (Sandoz Research Institute, New Jersey; [cis-(+/−)-1-[2-hydroxy[[tetrahydro-5-[(octadecylaminocarbonyl)oxy]methyl]-furan-2-yl]methoxy-phosphinyloxy]ethyl]quinolinium hydroxide, inner salt) and WEB 2086 (Boehringer Ingelheim; [3-[4-(2-chlorophenyl)-9-methyl-6H-thieno[3,2-f][1,2,4]-triazolo-[4,3a][1,4]diazepin-2-yl]-1-(4-morpholinyl)-1-propanone) were prepared as a 1 mg/ml stock solutions in phosphate buffered saline and Iloprost (Schering AG, Berlin, F.R.G.; [5-(E)-(1S,5S,6R.7R)-7-hydroxy-6-(E)-(3S,4RS)-3-hydroxy-4-methyl-oct-1-en-6-yn-yl-bicyclo 3.3.0-octano-3-yliden-pentanoic acid) as 0.1 mg Iloprost/ml saline. To produce the concentration of inhibitors required, serial dilution was performed with saline. The potency of the three inhibitors was tested in a platelet aggregation assay as previously described.

Catabolism Assay

This was performed as for Example 1, except that 45 μl of Tyrodes-BSA containing appropriate concentrations of inhibitors was added.

Lipid extraction and ion exchange chromatography were performed according to Example 1.

Results

Figure 3:
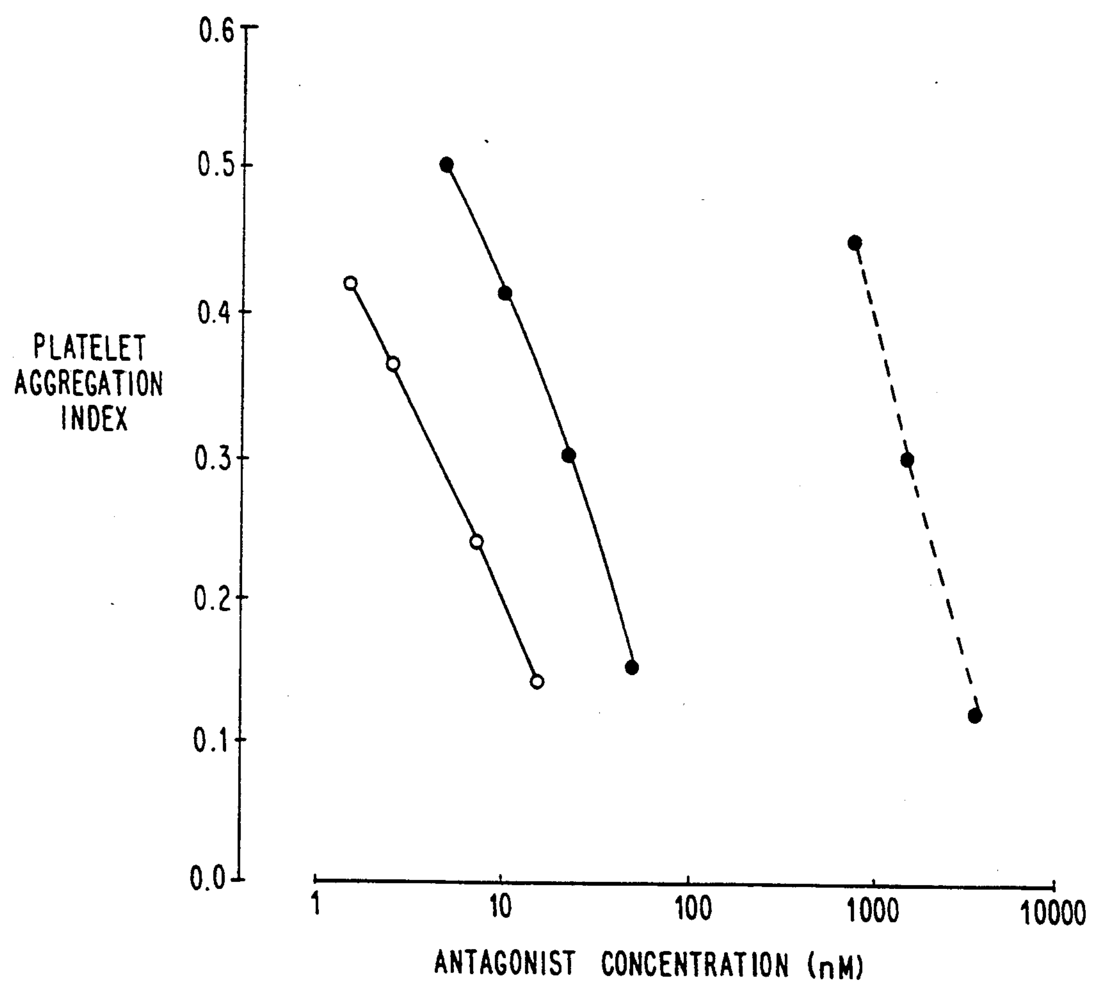
FIG. 3, shows the effect of antagonist concentration (nM) on the platelet aggregation index. ○——○ represents Iloprost, ●——● represents WEB 2086 and ●- - - -● represents SRI 63-441.

FIG. 3 shows the relative potency of inhibition of PAF induced platelet aggregation by the three antagonists used in this study. It can be seen that both Iloprost and WEB 2086 are markedly more potent than SRI 63-441 and Iloprost was significantly more potent than WEB 2086 (Iloprost $IC_{50}$ 13.9 nM and WEB 2086 $IC_{50}$ 55 nMO.

Figure 4:
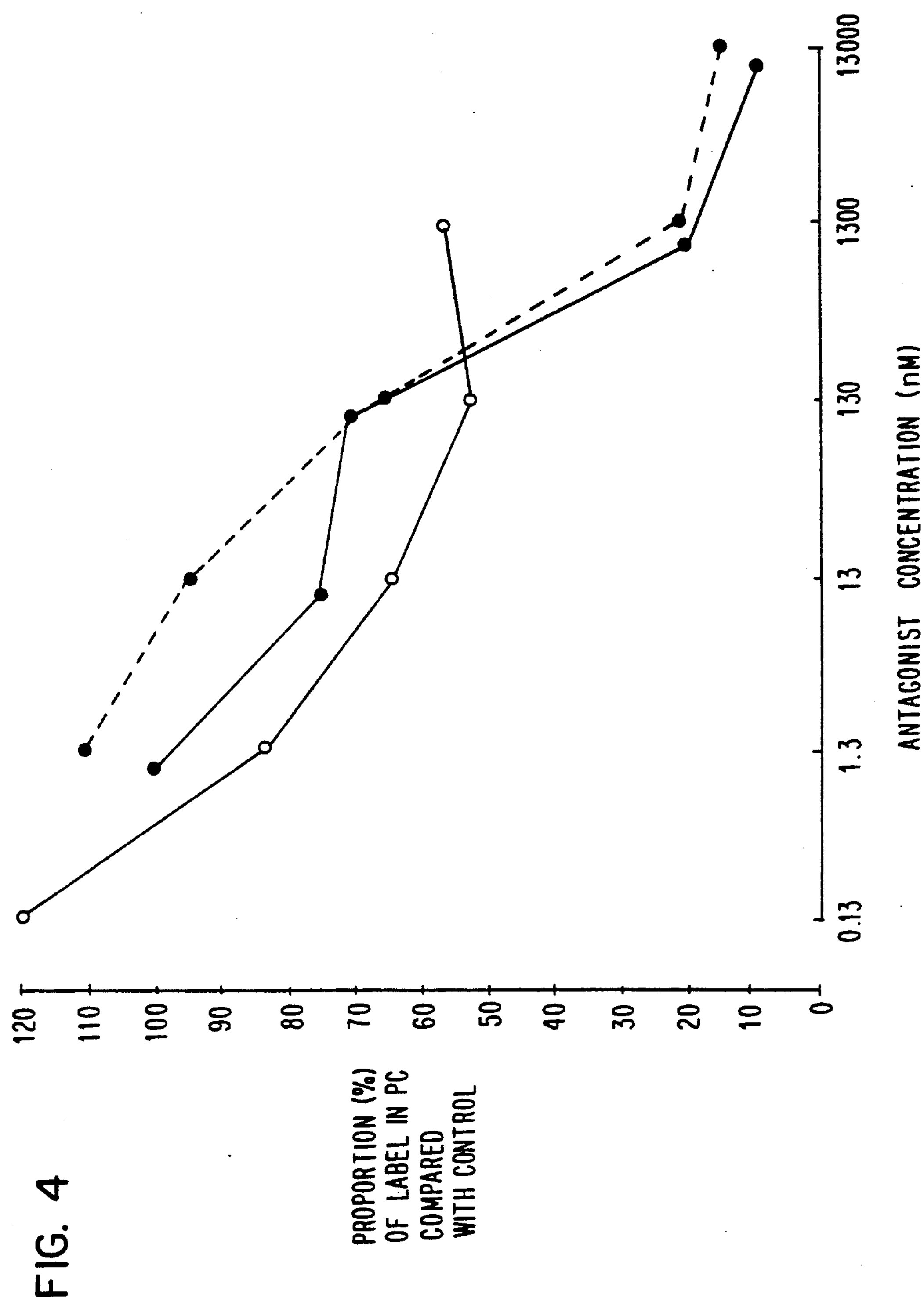
FIG. 4, shows the effect of antagonist concentration (nM) on the conversion of $^3$H-PAF to alkylacyl GPC. ○——○ represents Iloprost, ●——● represents WEB 2086 and ●- - - -● represents SRI 63-441.

FIG. 4 shows that the PAF receptor-antagonists SRI 63-441 and WEB 2086 caused an almost complete inhibition of conversion of $^3$H-PAF to alkylacyl GPC. There was little difference between the potency of, or slope of the response to the two antagonists, except that WEB 2086 was marginally more potent at low doses. From no response to maximum response required a 1,000 fold increase in the dose of antagonist. Iloprost caused significant inhibition of catabolism at lower doses than SRI 63-441 and WEB 2086. In contrast to the two-receptors antagonists, Iloprost caused only a maximum of approximately 50% inhibition compared with antagonist-free controls. WEB 2086 and SRI 63-441 caused a 90% inhibition of catabolism compared with controls. As with the receptor-antagonists, Iloprost displayed its maximum inhibitory effect at a 1,000-fold higher dose than its non-effective concentration.

EXAMPLE 3

The following example shows the results of a series of experiments where relatively high dose PAF receptor antagonists were administered to mice on days 1–4 of pregnancy. In all cases the control mice were given saline injections at the same time. The implantation rate of controls was very low due to stress. Stress was achieved by the crowding of animals.

In the example, the antagonists were given at 16:00 h on D1 and at 10:00 h on days 2–4. Necroscopies were performed on day 8 to determine the success of implantation. The antagonists were administered as 200 μl/30 g body weight. The diluent was phosphate buffered saline (PBS), pH 7.3. The antagonists were prepared in the following manner:

WEB 2086 (3-[4-(2-chlorophenyl)-9-methyl-6H-thienol(3,2-f[1,2,4]-triazolo-[4,3-a][1,4]-diazepin-2-yl]-1-(4-morpholinyl)-1-propanone (from boerhringer Ingelheim KG, FRG) was weighed from dry powder and dissolved directly into PBS.

BN 52021 Ginkgolide B; extract of Ginkgo Biloba (from IHB-IPSEN, Le Plessis Robinson, France) was dissolved in methanol and then diluted to a working concentration on PBS.

SRI 63 675 [cis-(+/−)-1-[2-[hydroxy]tetrahydrofuran-2,5-dimethyl-5-[9-octadecylaminocarbonyl)-oxy]-methyl]furan-2-yl]methoxyphosphinyloxylethyl-quinolinium hydroxide, inner salt (from Sandoz Research Institute, New Jersey, USA) was dissolved directly into PBS.

SRI 64 557 (from Sandoz, New Jersey) was also dissolved directly into PBS.

The results are shown in the following table.

TABLE 4

| Antagonist | Implantation Rate (%)* Control | Treated | Dose (μg) |
|---|---|---|---|
| WEB 2086 | 30.9 | 65.3 | 50 |
| | 38.0 | 25.3 | 100 |
| | | 26.6 | 150 |
| | 49.7 | 56.3 | 100 |
| | 26.5 | 55.8 | 100 |
| | 0 | 20.9 | 20 |
| | 30 | 41.8 | 10 |
| | 35.3 | 65.0 | 100 |
| | 5 | 63.2 | 10 |
| | 50 | 66 | 25 |
| | | 63 | 50 |
| | | 65 | 100 |
| | 38.6 | 59.8 | 10 |
| | | 78.9 | 25 |
| | | 60.9 | 50 |
| BN 52021 | 27.2 | 62.9 | 25 |
| | | 45.6 | 50 |
| | 21.7 | 20.1 | 25 |
| | | 26.0 | 50 |
| | 33.1 | 47.2 | 50 |
| | | 55.4 | 100 |
| SRI 63 675 | 47.4 | 69.2 | 100 |
| SRI 64 557 | 30.2 | 40.7 | 40 |

*All results for implantation rate are the mean of from 4 to 12 mice.

EXAMPLE 4

This study examines the contragestational and antiplatelet effects of the antagonists SRI 63-441, SRI 66-412, K 36-374, WEB 2086 and BN 52021.

For the contragestational study antagonists were given as intraperitoneal injections on days 1 to 4 of pregnancy and autopsies performed on day 8. The implantation rate was $$\frac{\text{Number of implantation sites}}{\text{Number of corpora lutea}} \times 100$$

The antiplatelet effects were performed with a platelet aggregation assay using rabbit citrated blood, in which the antagonists were inhibitory at all doses tested. No evidence of partial agonism even at extremely high doses was found.

Figure 5A:
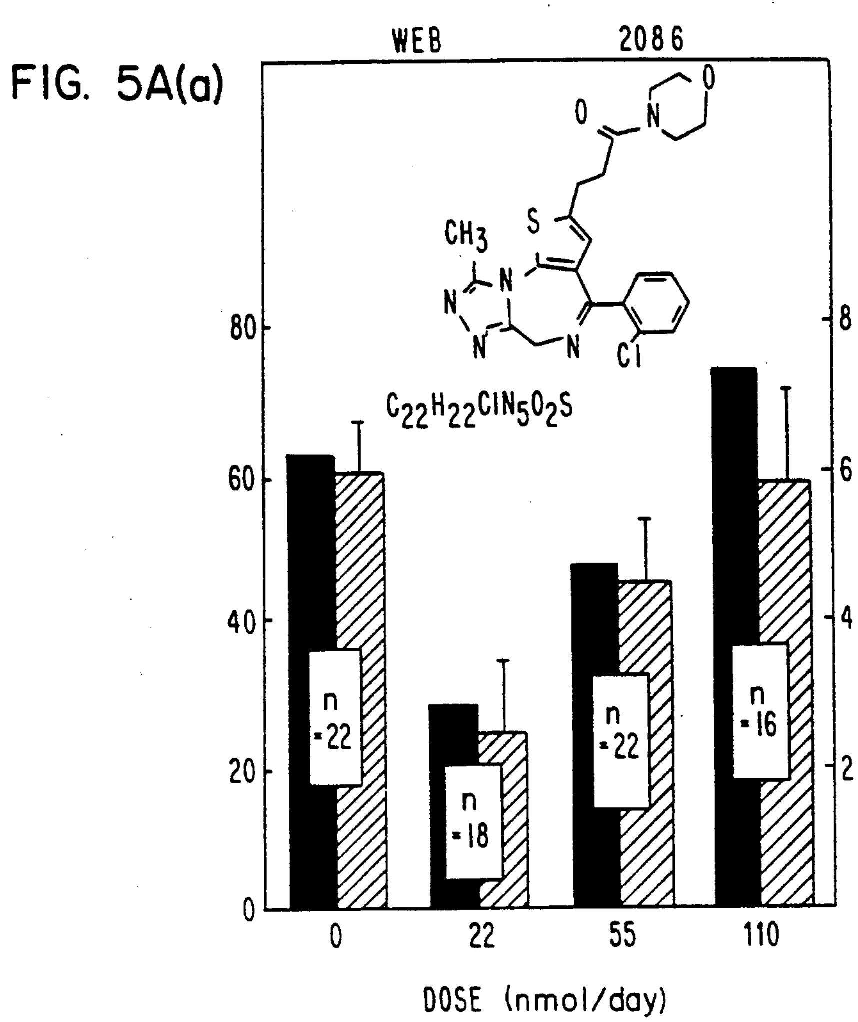
FIG. 5*a* and 5*b*, show the effect of PAF antagonists WEB 2086 and BN 52021, respectively, on the implantation rate of mouse embryos, and in an in vitro platelet aggregation assay.
Figure 5A:
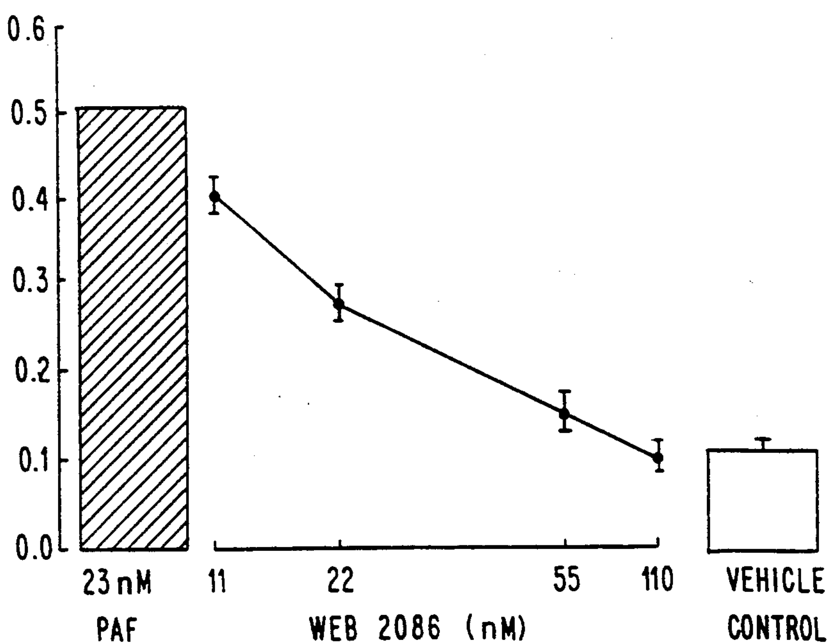
Figure 5B:
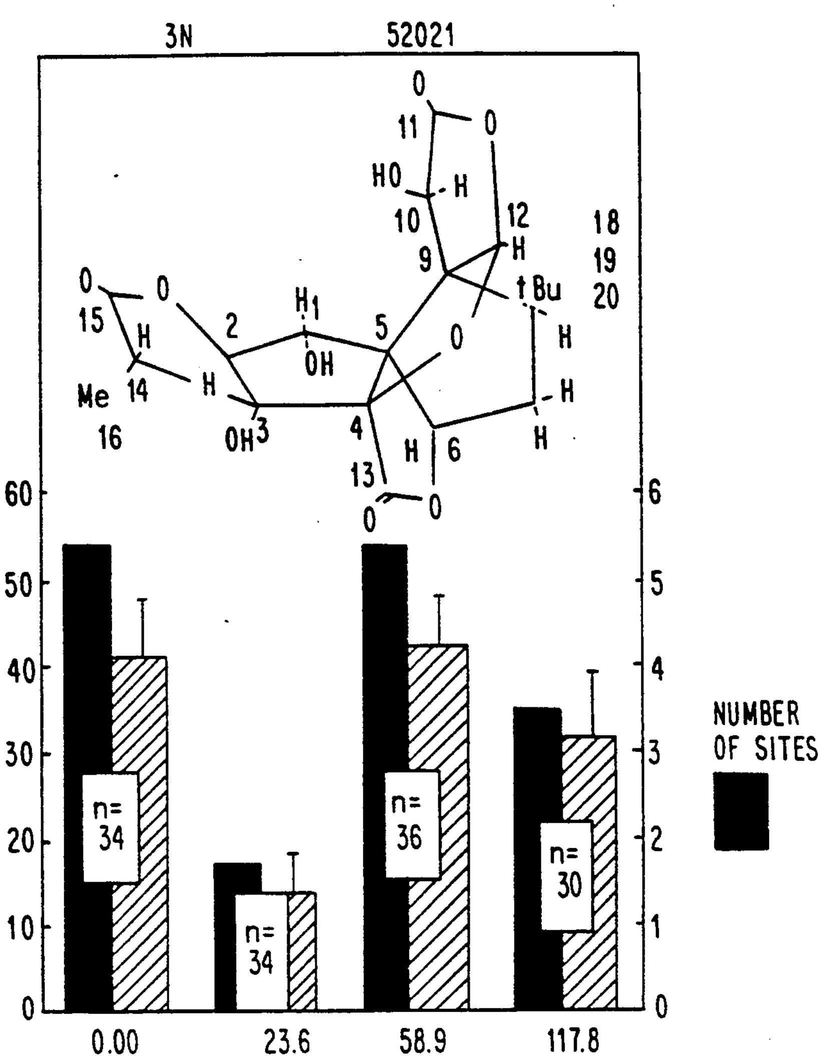
Figure 5B:
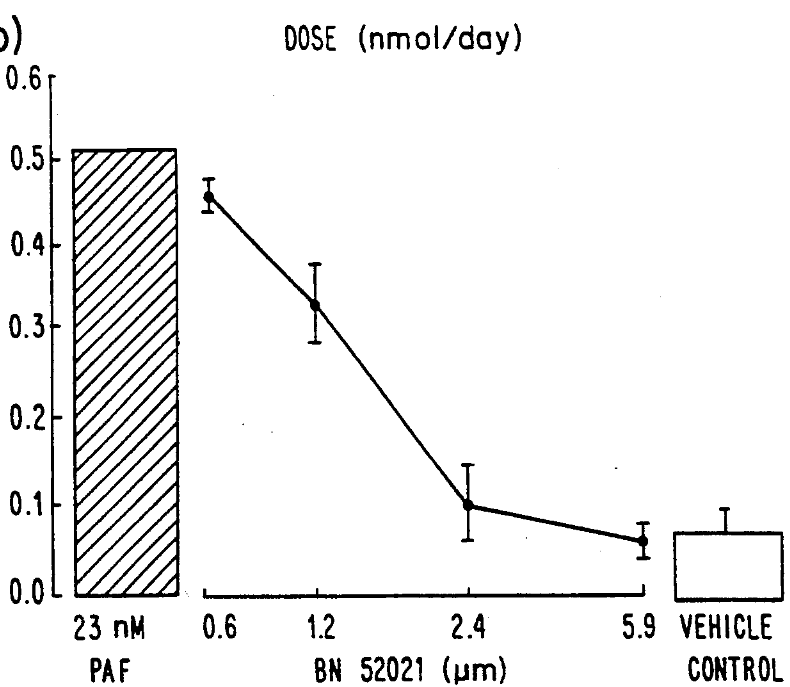

The dose-dependent effects of antagonists WEB 2086 and BN 52021 on mouse embryo implantation and in an in vitro platelet aggregation assay are illustrated in FIGS. 5a and 5b, respectively.

Figure 6A:
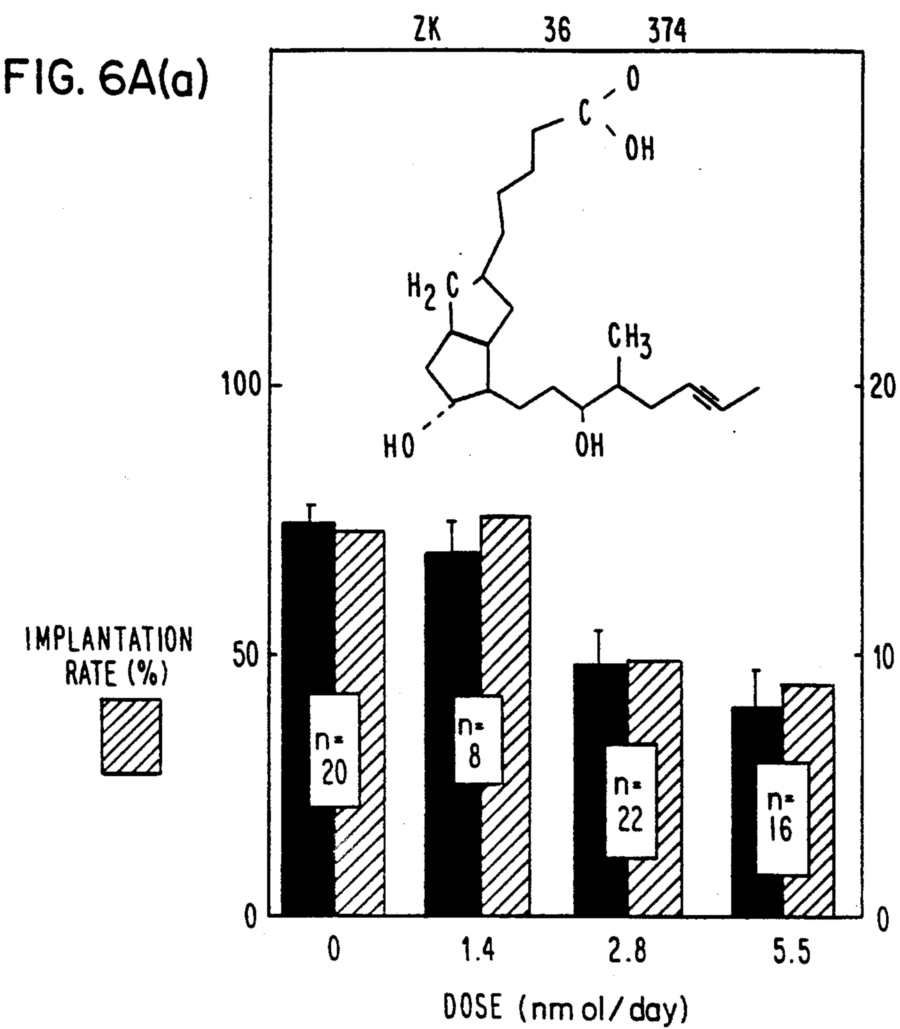
FIG. 6*a*, 6*b* and 6*c* show the effect of PAF antagonists ZK 36-374, SRI 63-441 and SRI 64-412, respectively, on the implantation rate of mouse embryos and in an in vitro platelet aggregation assay.
Figure 6A:
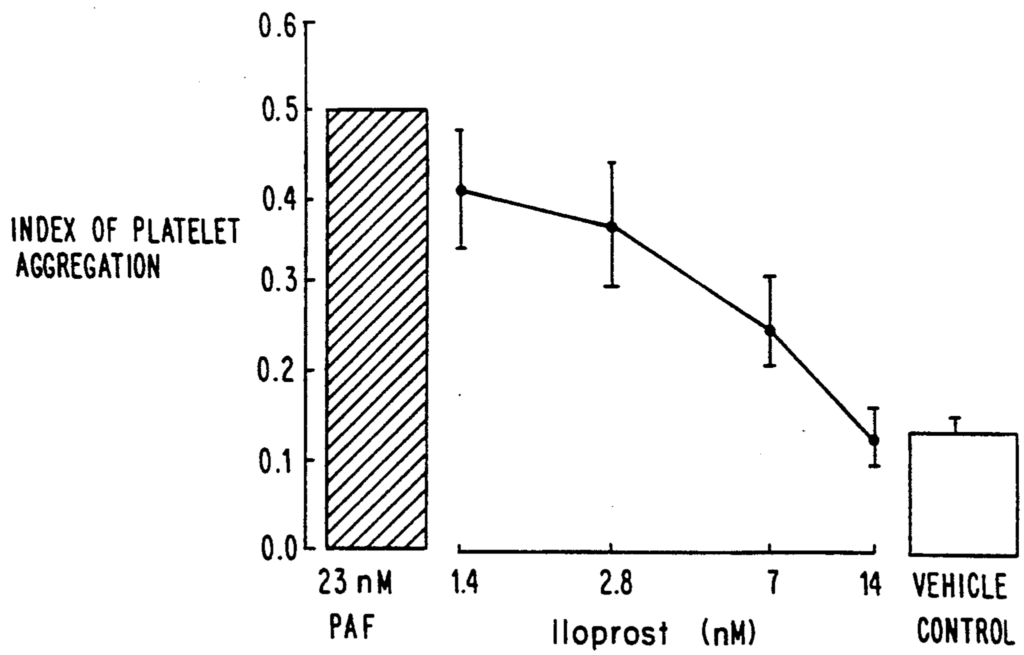
Figure 6B:
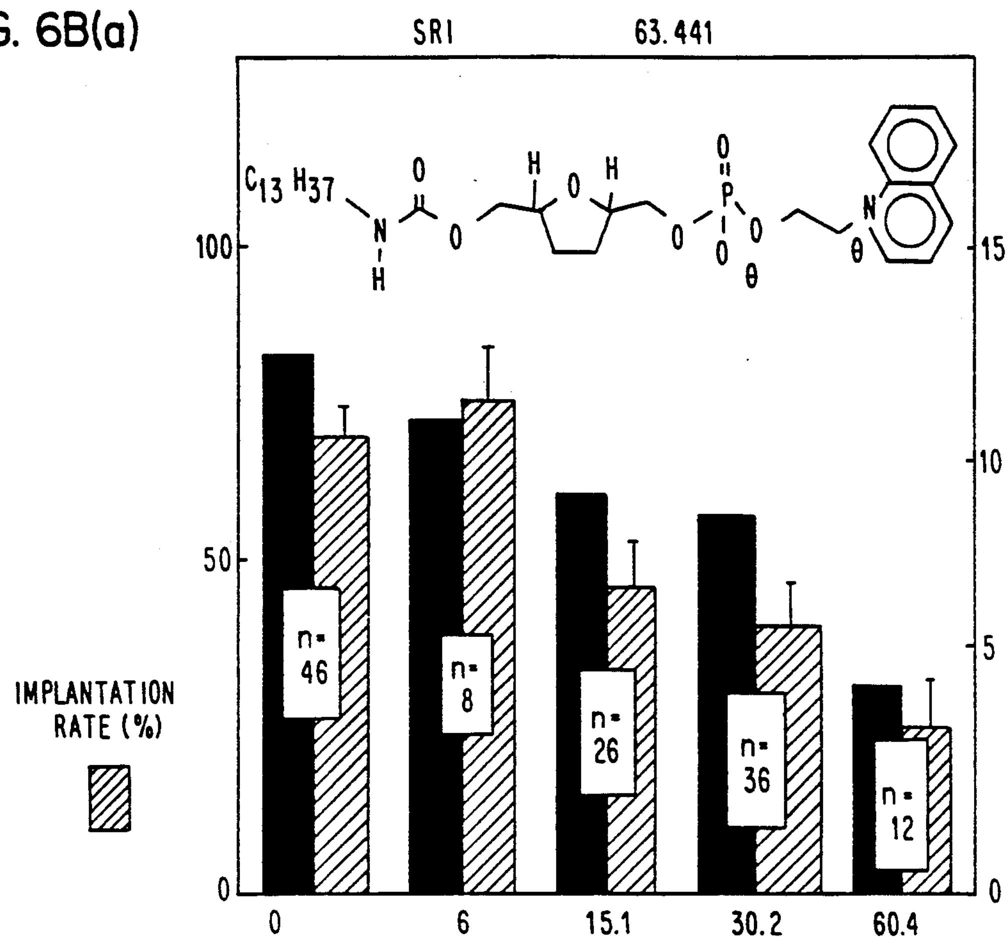
Figure 6B:
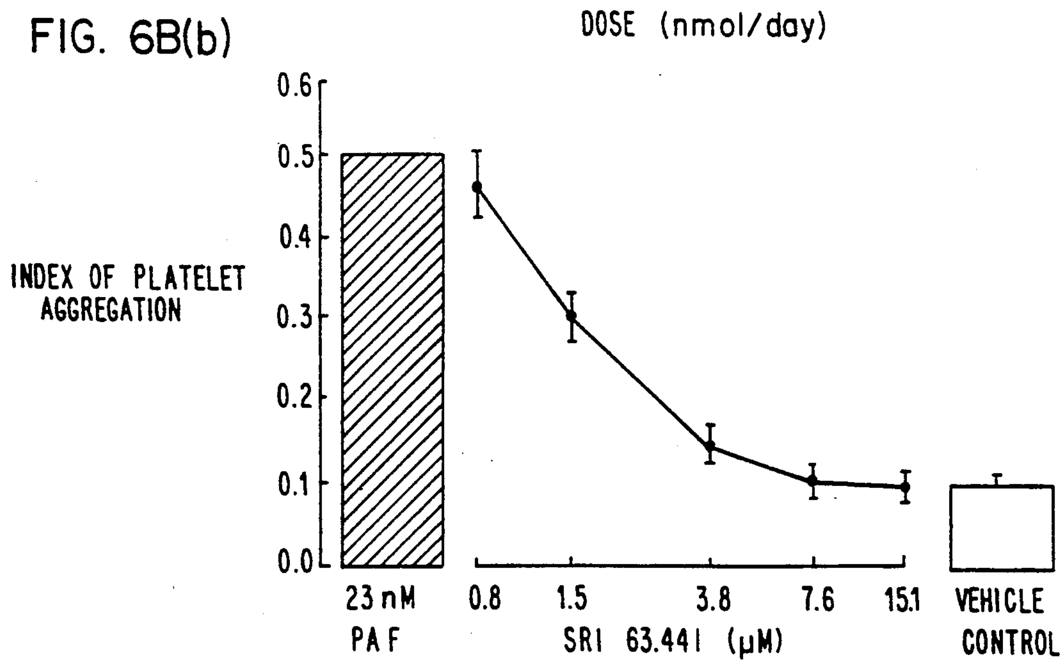
Figure 6C:
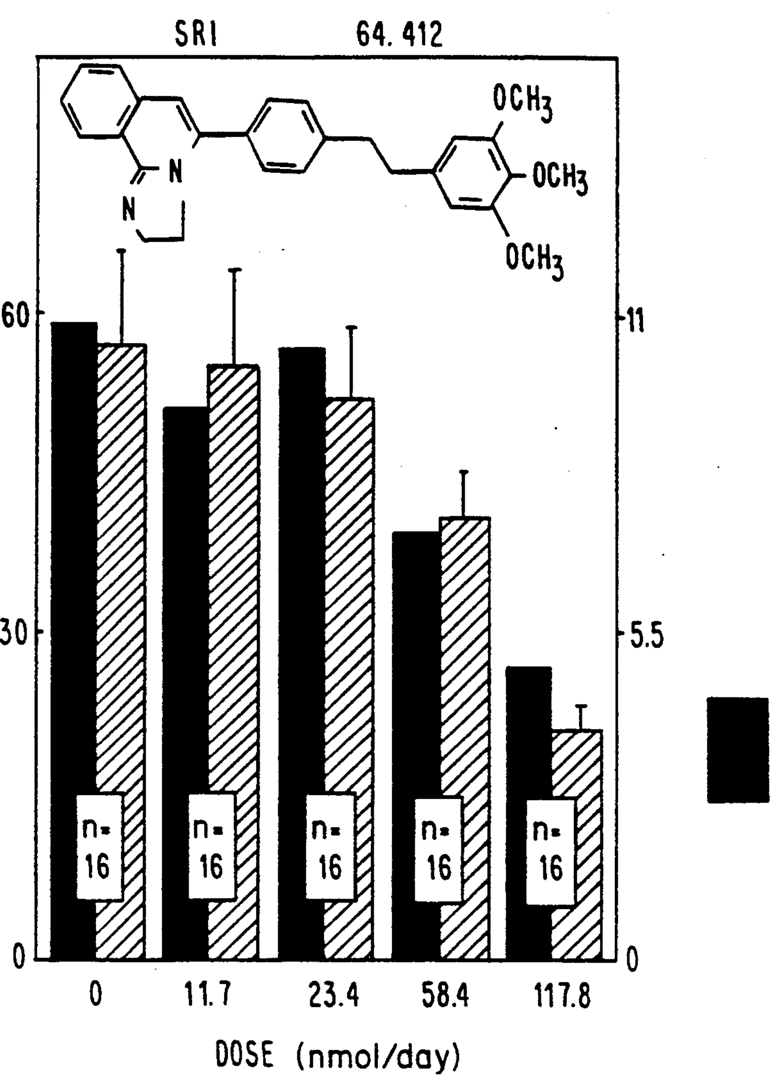
Figure 6C:
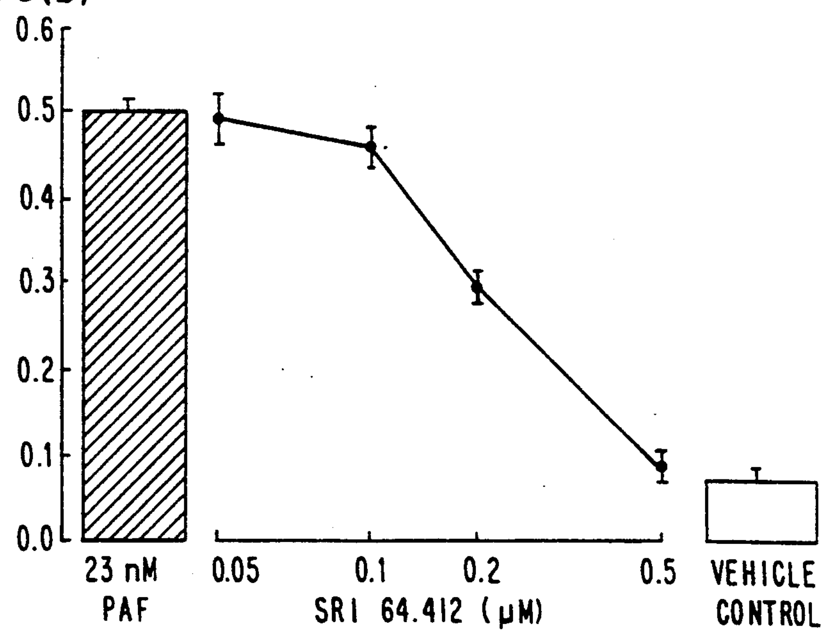
Figure 5B:
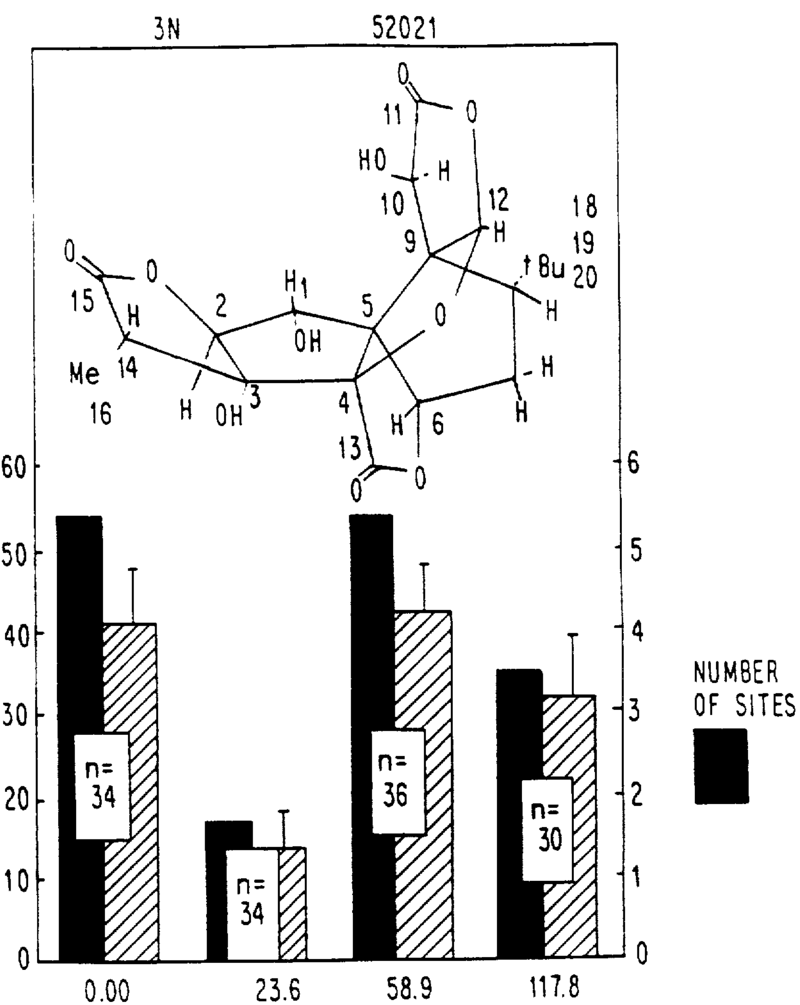
Figure 5B:
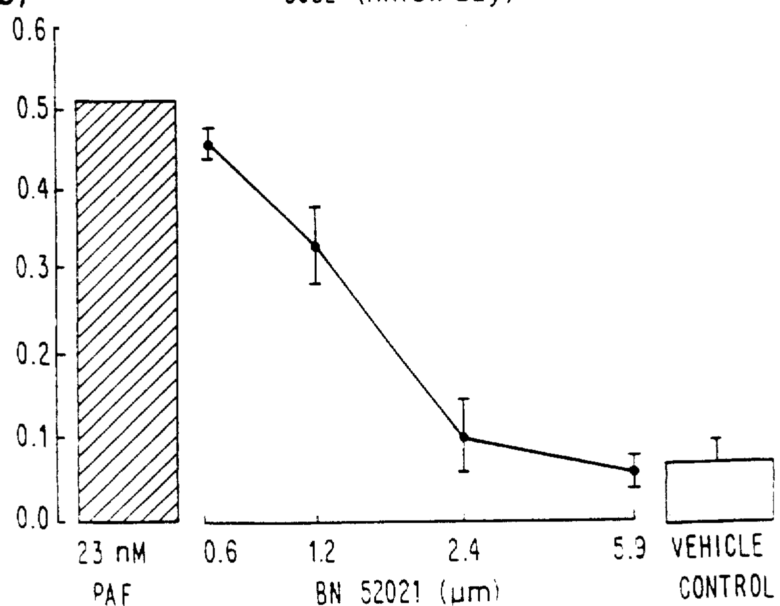
Figure 6A:
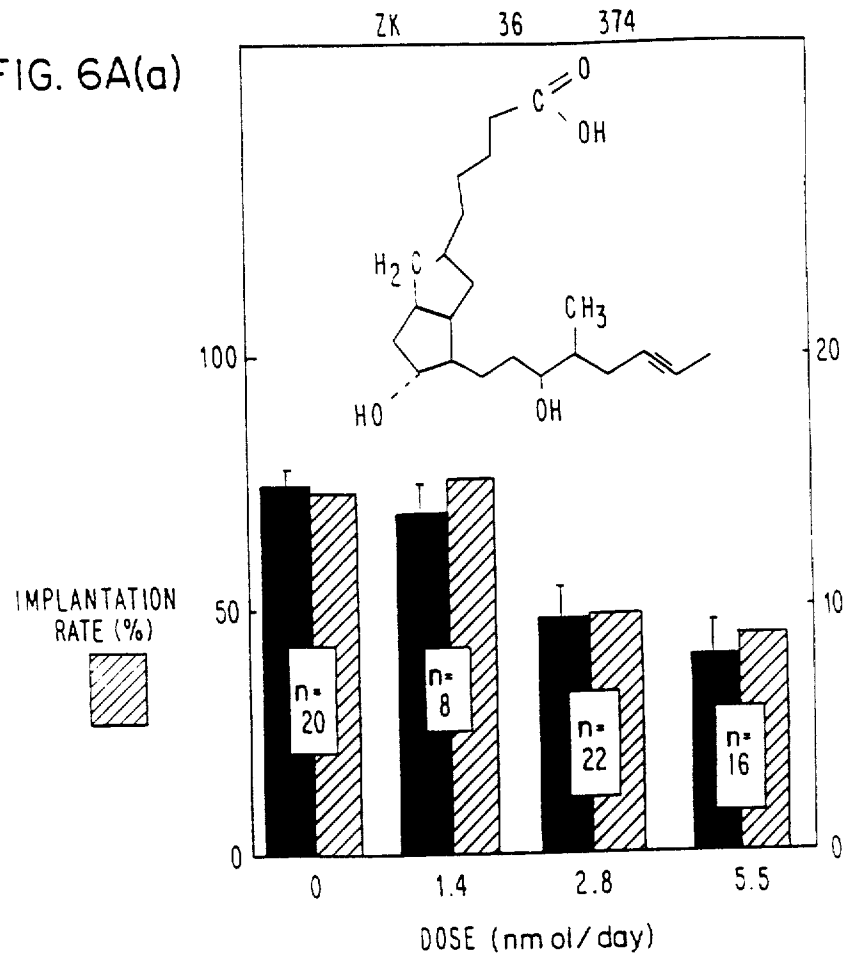
Figure 6A:
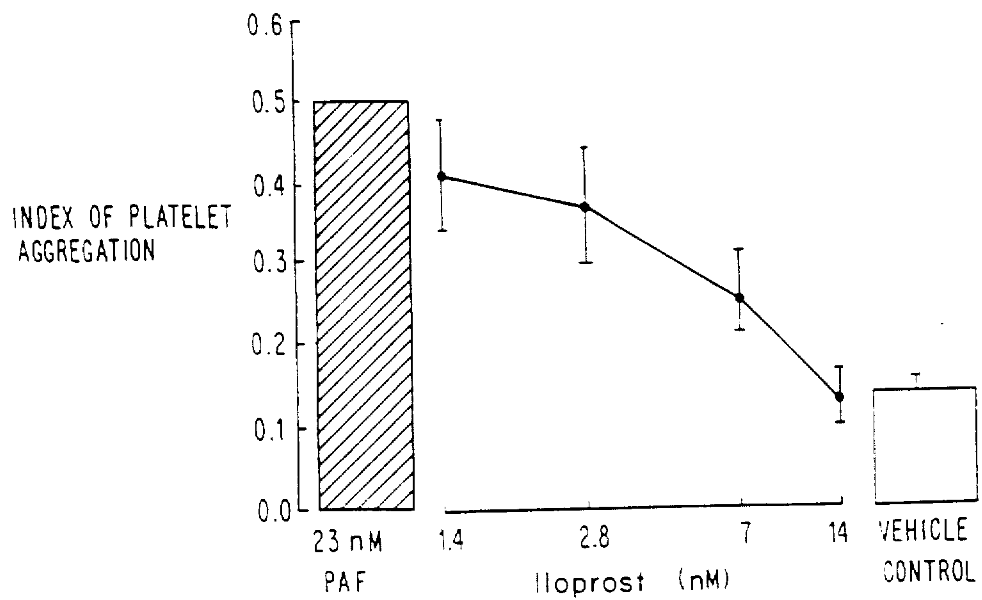

FIGS. 6a 6b and 6c show the effects of the PAF antagonists ZK 36-374, SRI 63-441 and SRI 64-412 in an in vitro platelet aggregation assay and on the implantation rate of mouse embryos. The PAF antagonists all have unrelated structures, SRI 63-441 is related to the PAF structure but the others are not. Their antiplatelet activity showed considerable dosedependent differences with the activity ranking

ZK 36-374>WEB 2086>SRI 64-412>BN 52021>SRI 63-441

However this rank was different from their contragestational action

ZK 36-374>WEB 2086>BN 52021>SRI 63-441>SRI 64-412.

It is apparent that for a number of the antagonists the anti-implantation effects were restricted to a relatively narrow dose range, after which the antagonism was lost. However, this pattern of response for implantation was entirely different from that observed for platelet aggregation. The unexpected result for implantation further suggests that the embryo's responses to PAF antagonists are different from the platelets.

EXAMPLE 5

The following table shows the results of administering 100 μg of the PAF receptor antagonist WEB 2086 together with 2 μg of synthetic PAF on days 1-4 of pregnancy in mice induced to have a poor implantation rate.

TABLE 5

| Control | WEB ALONE Implantation Rate (%) | WEB + PAF |
|---|---|---|
| 25.1 | 42.0 | 65.3 |
| 33.9 | 51.7 | 60.4 |
| 36.8 | 63.1 | 71.1 |

EXAMPLE 6

The following results refer to the implantation pregnancy rate of mice following embryos transfer on day 3 of embryos grown in culture for 3 days. The recipients were treated with either saline or PAF-antagonists plus synthetic PAF as described above. The numeral in brackets refers to the number of animals tested.

| IMPLANTATION RATE (%) | |
|---|---|
| Control | WEB + PAF |
| 43.2 (12) | 67.5 (15) |

EXAMPLE 7

The following example, provides evidence of a direct autocrine effect of PAF of the embryo.

Evidence that embryo-derived PAF may be exerting its actions at the embryonic level was obtained from metabolic studies. The production of $CO_2$ from lactate labelled at the C-1 position, reflecting the rate of substrate entry into the TCA cycle, was used. Two-cell embryos cultured in media supplemented with 1.0 μg PAF/ml produced 18% more $CO_2$ from lactate than did controls. At higher doses it resulted in a more variable response with a reduction in the production of $CO_2$. Culture of embryos in media supplemented with PAF did not significantly increase the proportion of embryos developing to the expanded blastocyst stage. However, expanded blastocysts cultured for 72 h in media supplemented with 1.0 μg PAF/ml produced 30% more $CO_2$ from lactate than did controls.

This effect was due to the presence of PAF during culture and not to the influence of residue PAF during the $CO_2$ production assay, since a further increase in $CO_2$ output was observed if PAF was present in the assay media. This increase in embryo metabolism was paralleled by an increase in cell number of the embryos. This increase in embryo metabolism was paralleled by an increase in cell number of the embryos. The result suggests that embryos, unlike most other cells studied to date, do not undergo down-regulation of PAF mediated effects.

EXAMPLE 8

This increase in the metabolic rate of embryos was translated into an increase in the pregnancy potential of the embryos. Two-cell embryos were cultured for 72 h in the presence or absence of PAF. They were then transferred to uteri of pseudopregnant foster mothers. Supplementation of media with 0.1 μg/ml PAF resulted in a 54% increase ($p<0.001$) in the implantation rate above controls. Calculation of between animal variation was made possible by the transfer of control embryos to one uterine horn and treated embryos to the other. After correcting for significant between animal variation, the significant effect of PAF supplementation in media remained evident, demonstrating that the enhanced implantation rate was solely due to the enhanced viability of embryos. Thus PAF appears to have a direct autocrine effect on the preimplantation stage embryo which enhances its ability to implant.

EXAMPLE 9

Description of Experiment

Mice of the Quackenbush Strain, 8-10 weeks of age were induced to undergo superovulation with 3 international units of pregnant mare serum gonadotrophin and 48 h later 3 international units of human chorionic gonadotrophin. They were then left with males of proven fertility overnight and the presence of the copulatory plug was confirmed the following morning (day 1 of pregnancy).

Mice were assigned to one of three groups, (1) injections of phosphate buffered saline supplemented with 3 mg bovine serum albumin/ml (PBS-BSA), (2) injections of 25 μg WEB 2086 in PBS-BSA, and (3) injections of 25 μg WEB 2086 plus 5 μg PAF in PBS-BSA. All injections were intraperitoneal in a volume of 200 μl. The injections were given at 16:00 on days 1-4 of pregnancy.

On day 17 of pregnancy, necroscopies were performed. The fetoplacental unit was dissected away from the uterus and the morphology and the number of viable fetuses was recorded, as were the number of resorption sites and the fetal and placental weights.

The results as shown in the accompanying tables indicate that such treatment with a high dose of antagonist either in the presence or absence of exogenous PAF resulted in:

Significantly increased implantation rate

Significantly increased proportion of implanted embryos continuing development to viable fetuses.

A significant increase in the weight of fetuses and thus presumably their growth rates.

No increase in the incidence of fetal abnormalities.

The addition of exogenous PAF seemed to have a modest potentiation of the effects of the inhibitor alone.

TABLE 6

| | Control | WEB 2086 | WEB 2086 + PAF |
|---|---|---|---|
| Implant Rate | 17.91 ± 1.3 | 19.40 ± 0.8* | 21.1 ± 1.0* |
| Proportion of implanted fetuses viable on day 17 | 70.1% | 81.2%** | 82.1%** |
| Expected litter | 12.6 | 15.75 | 17.3 |
| Proportion increase compared with control | | 25% | 37.3% |

*$p < 0.05$ compared to control by analysis of variance
**$p < 0.05$ compared to control by $X^2$

TABLE 7

| MEAN FETAL WEIGHT (means ± S.D.) (number of fetuses examined) | | |
|---|---|---|
| Control | WEB 2086 25 μg | 25 μg + 10 μg PAF |
| 0.636 ± 0.091 (387) | 0.669 ± 0.118* (529) | 0.670 ± 0.109* (431) |

*$p < 0.001$ compared to control by analysis of variance

I claim:

1. A method of enhancing implantation of an embryo within the uterus of a female mammal which method comprises administering to said mammal an effective implantation enhancing amount of a synthetic PAF antagonist.

2. The method according to claim 1 wherein the mammal is selected from the group consisting of human, bovine, ovine, equine, porcine, caprine, canine and feline mammals.

3. The method according to claim 1 wherein the synthetic antagonist is selected from the group consisting of alprazolam, triazolam, brotizolam, etizolam, WEB 2086, STY 2108, WEB 2170, diltiazem and verapamil.

4. The method according to claim 3 wherein the synthetic PAF antagonist is WEB 2170 or WEB 2086.

5. The method according to claim 1 wherein the synthetic PAF antagonist is administered during the pre-and peri-implantation period of pregnancy.

6. The method according to claim 5 wherein the synthetic PAF antagonist is administered together with PAF, wherein the antagonist is administered systemically and PAF is administered systemically or locally.

7. The method according to claim 6 wherein the mammal is a human and the synthetic PAF antagonist, together with PAF is administered on days 1 to 7 of pregnancy.

8. The method according to claim 7 wherein the embryo has been cultured in vitro prior to implantation.

9. A method of increasing the level of PAF around an embryo in the uterus of a female mammal, which method comprises administering to the mammal an amount of a synthetic PAF antagonist sufficient to inhibit PAF catabolism.

10. The method according to claim 9 wherein the mammal is selected from the group consisting of human, bovine, ovine, equine, porcine, caprine, canine and feline mammals.

11. The method according to claim 9 wherein the synthetic antagonist is selected from the group consisting of alprazolam, triazolam, brotizolam, etizolam, WEB 2086, STY 2108, WEB 2170, diltiazem and verapamil.

12. The method according to claim 11 wherein the synthetic PAF antagonist is WEB 2170 or WEB 2086.

13. The method according to claim 9 wherein the synthetic PAF antagonist is administered during the pre- and peri-implantation period of pregnancy.

14. The method according to claim 13 wherein the synthetic PAF antagonist is administered together with PAF, wherein the antagonist is administered systemically and PAF is administered systemically or locally.

15. The method according to claim 14 wherein the mammal is a human and the synthetic PAF antagonist, together with PAF is administered on days 1 to 7 of pregnancy.

16. The method according to claim 15 wherein the embryo has been cultured in vitro prior to implantation in the mammal.

17. A composition for enhancing implantation of an embryo within the uterus of a female mammal comprising, an effective implantation enhancing amount of synthetic PAF antagonist together with PAF.

18. The composition according to claim 17 wherein the synthetic antagonist is selected from the group consisting of alprazolam, triazolam, brotizolam, etizolam, WEB 2086, STY 2108, WEB 2170, diltiazem and verapamil.

19. The composition according to claim 18 wherein the PAF antagonist is WEB 2170 or WEB 2086.

20. A composition according to claim 17 further comprising a pharmaceutically acceptable carrier, diluent, excipient and/or adjuvant.

21. A process of preparing a composition according to claim 20, comprising mixing a synthetic PAF antagonist and PAF with a pharmaceutically acceptable carrier, diluent, excipient and/or adjuvant.

* * * * *

UNITED STATES PATENT AND TRADEMARK OFFICE
CERTIFICATE OF CORRECTION

PATENT NO. : 5,240,922
DATED : Aug. 31, 1993
INVENTOR(S) : Christopher O'Neill

It is certified that error appears in the above-indentified patent and that said Letters Patent is hereby corrected as shown below:

In the drawings, sheets 6 and 7, consisting of Figs. 5B(a) and 6A(a), should be deleted to be replaced with the corrected Figs. 5B(a) and 6A(a), as shown on the attached pages.

Signed and Sealed this

Seventh Day of June, 1994

Attest:

BRUCE LEHMAN

*Attesting Officer*

*Commissioner of Patents and Trademarks*

DOSE (nmol/day)

ZK 36 374
IMPLANTATION
RATE (%)
100
50
0
20
10
n= 20
n= 8
n= 22
n= 16
0
1.4
2.8
5.5
DOSE (nmol/day)

INDEX OF PLATELET
AGGREGATION
0.6
0.5
0.4
0.3
0.2
0.1
0.0
23 nM
PAF
1.4
2.8
7
14
Iloprost (nM)
VEHICLE
CONTROL